United States Patent [19]

Sugawara et al.

[11] Patent Number: 5,093,248

[45] Date of Patent: Mar. 3, 1992

[54] BU-3862T ANTITUMOR ANTIBIOTIC

[75] Inventors: Koko Sugawara, Wako; Masami Hatori, Yokosuka; Hideo Kamei, Tokyo; Masataka Konishi, Kawasaki; Toshikazu Oki, Yokohama; Koji Tomita, Tokyo, all of Japan

[73] Assignee: Bristol-Myers Squibb Co., New York, N.Y.

[21] Appl. No.: 438,281

[22] Filed: Nov. 13, 1989

Related U.S. Application Data

[62] Division of Ser. No. 165,337, Mar. 7, 1988, Pat. No. 4,912,133.

[51] Int. Cl.$^5$ .......................... C12P 17/02; C12P 7/24; C12P 7/02; C12N 1/20
[52] U.S. Cl. .................................... 435/123; 435/147; 435/155; 435/898; 435/253.5
[58] Field of Search ..................... 435/123, 898, 253.5, 435/147, 155

[56] References Cited

U.S. PATENT DOCUMENTS 3,271,253 9/1966 Price ................................ 435/898
3,595,955 7/1971 DeBoer ............................. 435/898

OTHER PUBLICATIONS

Miyano et al., *J. Antibiot*, vol. 25, pp. 489–491, 1972.

*Primary Examiner*—Douglas W. Robinson
*Assistant Examiner*—Irene Marx
*Attorney, Agent, or Firm*—David M. Morse

[57] ABSTRACT

A new antitumor antibiotic designated herein as BU-3862T is produced by fermentation of *Streptomyces hygroscopicus* ATCC 53709. BU-3862T and its diacetyl and dihydro derivatives inhibit the growth of tumors in experimental animals.

1 Claim, 3 Drawing Sheets

BU-3862T ANTITUMOR ANTIBIOTIC

This is a division of our prior co-pending application Ser. No. 165,337 filed Mar. 7, 1988, now U.S. Pat. No. 4,912,133.

BACKGROUND OF THE INVENTION

1. Field of the Invention

This invention relates to novel antitumor antibiotics and to their production and recovery.

2. Description of the Prior Art

The present invention provides a novel fermentation product designated BU-3862T (I) which has the structure

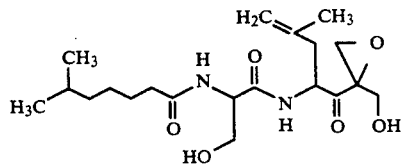

Also provided are the diacetate (II) and dihydro (III) derivatives of BU-3862T which have the structures shown below.

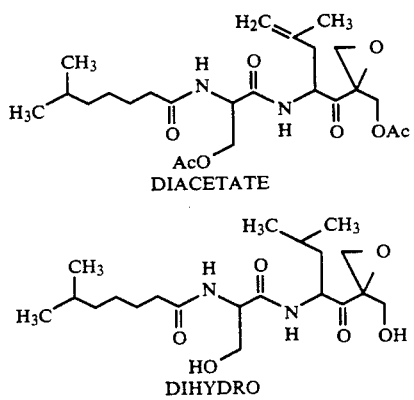

Applicants are not aware of any antitumor antibiotics related in structure to the compounds of the present invention.

SUMMARY OF THE INVENTION

This invention relates to a new antitumor antibiotic designated herein as BU-3862T which has the structural formula

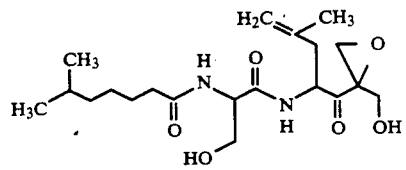

and to the process for the preparation, isolation and purification of BU-3862T.

The antibiotic of the present invention is obtained by fermentation of a BU-3862T-producing strain of *Streptomyces hygroscopicus*, preferably *Streptomyces hygroscopicus* strain P247-71 (ATCC 53709) or a mutant or variant thereof, in an aqueous nutrient medium under submerged aerobic conditions until a substantial amount of BU-3862T is produced by said organism in said culture medium and, optionally, recovering the BU-3862T from the culture medium.

Also provided are the diacetyl derivative of BU-3862T having the formula

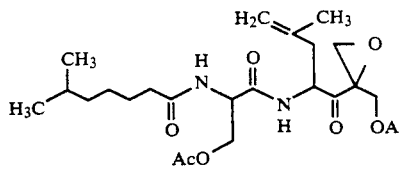

wherein Ac=$CH_3CO-$ which is produced by acetylation of BU-3862T and the dihydro derivative of BU-3862T having the formula

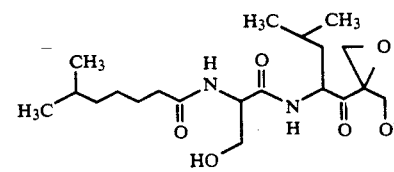

produced by catalytic hydrogenation of BU-3862T.

BU-3862T and its diacetyl and dihydro derivatives exhibit inhibitory activity against experimental animal tumor systems, e.g. B16 melanoma in mice.

DETAILED DESCRIPTION

Figure 1:
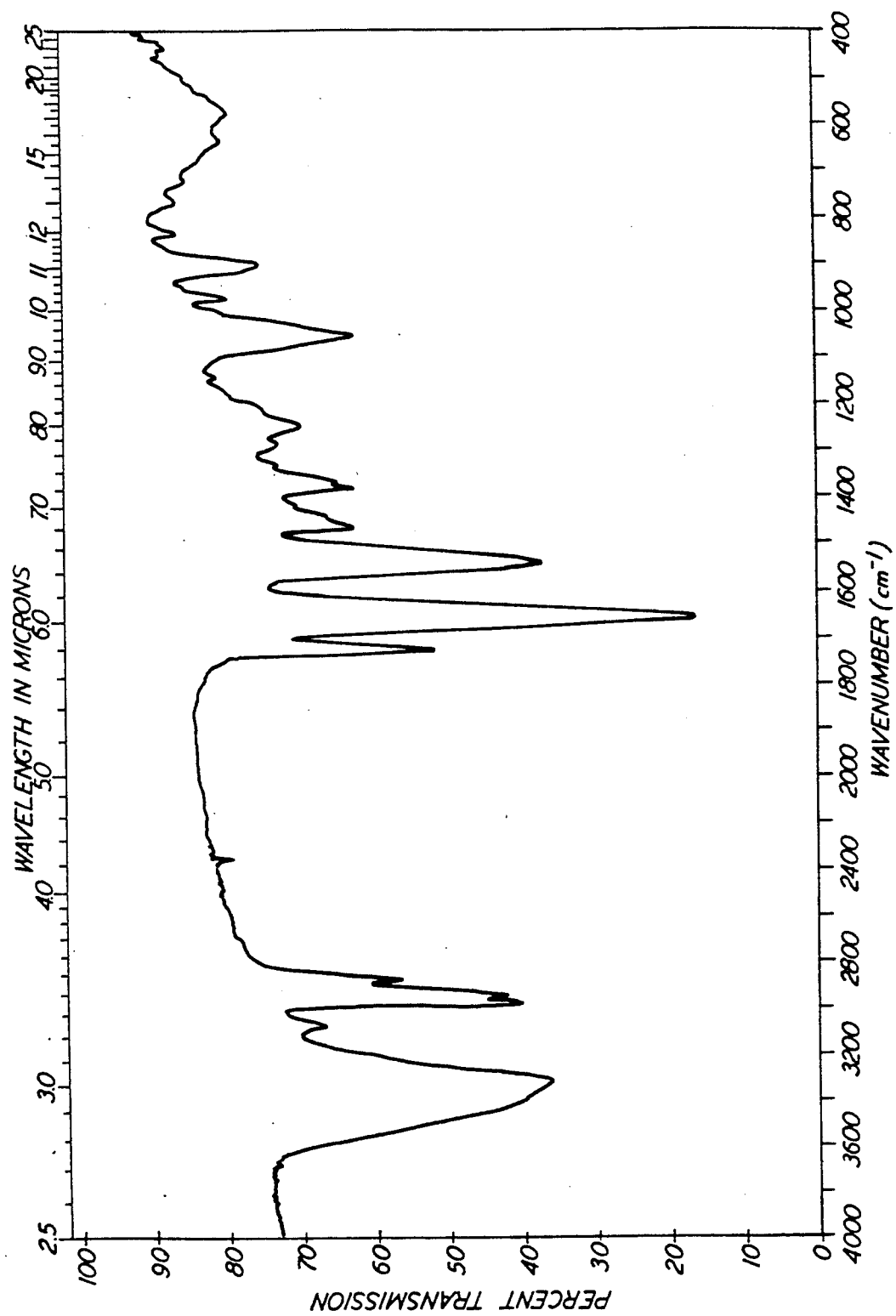
FIG. 1 represents the infrared absorption spectrum of BU-3862T (KBr).

The BU-3862T antibiotic of the present invention is produced by fermentation of a BU-3862T-producing strain of *Streptomyces hygroscopicus*.

A preferred BU-3862T-producing strain designated P247-71 was isolated from a soil sample collected near the root of a tamarind at Mt. Apo, Davao, Mindanao Island, the Philippines. A biologically pure culture of this strain has been deposited in The American Type Culture Collection, Rockville, Md.; and added to their permanent collection of microorganisms as ATCC 53709.

The results of taxonomic studies performed on strain P247-71 indicate that the strain belongs to the genus Streptomyces and to the species group *Streptomyces hygroscopicus*.

Strain P247-71 has the following properties:

MORPHOLOGY

Both substrate and aerial mycelia are formed. They are long, well-branched and not fragmented into short filaments. Chains of arthrospores are born on the aerial hyphae. The spore chains and spore morphology are as follows: 1) spiral spore chains with 2 to 8 turns, 2) monopodially branched sporophores, 3) spores, oval or barrel-shaped (0.5 to 0.7 by 0.5 to 1.2 μm), and 4) spore ornamentation, rugose or smooth.

Sporangium, motile spore and sclerotium are not observed.

CULTURAL AND PHYSIOLOGICAL CHARACTERISTICS

Strain P247-71 grows well in most descriptive media. Gray aerial mycelium with hygroscopic black patches is observed on ISP agar media except for ISP No. 6 medium. White to pale yellowish-gray aerial mycelium is formed on Czapek's sucrose-nitrate agar. The substrate mycelium is colorless or yellowish brown to grayish yellow. Melanin and other diffusible pigments are not produced. Most sugars are utilized for growth. The cultural and physiological characteristics are shown in Tables 1 and 2, respectively.

The morphological, cultural and physiological characteristics of strain P247-71 indicate that the strain belongs to the genus Streptomyces. According to the descriptions of Pridham and Tresner[1], the major characteristics of the strain are summarized as follows: 1) gray aerial mycelium, 2) spiral spore chain, 3) absent melanoid, and 4) smooth spore wall ornamentation. The hygroscopic change of sporulated aerial mycelium is a distinct property of the strain. The major characteristics and those shown in Tables 1 and 2 of strain P247-71 place it in *Streptomyces hygroscopicus*.

[1]Pridham, T. G. and H. D. Tresner: Genus Streptomyces Waksman and Henrici, 1943, p. 748-829. In R. E. Buchanan and N. E. Gibbons (ed.), Bergey's Manual of Determinative Bacteriology, 8th ed. 1974. The Williams & Wilkins Co., Baltimore.

It is to be understood that the present invention is not limited to use of the particular preferred strain P247-71 described above or to organisms fully answering the above descriptions. It is especially intended to include other BU-3862T-producing variants or mutants of the said organism which can be produced by conventional means such as x-ray radiation, ultraviolet radiation, treatment with nitrogen mustards, phage exposure and the like.

PREPARATION OF BU-3862T

BU-3862T may be produced by cultivating a BU-3862T-producing strain of *Streptomyces hygroscopicus*, preferably a strain having the characteristics of *Streptomyces hygroscopicus* strain P247-71 (ATCC 53709), or a variant or mutant thereof, under submerged aerobic conditions in an aqueous nutrient medium. The organism is grown in a nutrient medium containing an assimilable carbon source, e.g. glycerol, D-ribose, L-rhamnose, D-glucose, D-fructose, sucrose, lactose, melibiose, D-mannitol or soluble starch. The nutrient medium should also contain an assimilable nitrogen source such as fish meal, peptone, soybean flour, peanut meal, cottonseed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate or like ions.

Production of BU-3862T can be effected at any temperature conducive to satisfactory growth of the organ-

TABLE 1

Cultural characteristics of strain P247-71

| Medium | Growth | Aerial mycelium | Substrate mycelium | Diffusible pigment |
|---|---|---|---|---|
| Sucrose-nitrate agar (Czapek-Dox agar) | Moderate | Moderate; white to pale yellowish gray | Strong yellowish brown (74) | None |
| Tryptone-yeast extract broth (ISP No. 1) | Moderate; not turbid, floccose | None | Colorless | None |
| Yeast extract-malt extract agar (ISP No. 2) | Good | Scant; light gray (264) to black. Hygroscopic | Pale orange yellow (70) | None |
| Oat meal agar (ISP No. 3) | Poor | Poor; light gray (264) | Greenish gray (155) | None |
| Inorganic salts-starch agar (ISP No. 4) | Moderate | Moderate; light gray (264) | Colorless | None |
| Glycerol-asparagine agar (ISP No. 5) | Moderate | Moderate; brownish black (65). Hygroscopic | Colorless | None |
| Peptone-yeast extract-iron agar (ISP No. 6) | Poor | None | Colorless | None |
| Tyrosine agar (ISP No. 7) | Moderate | Moderate; dark gray (266) | Dark grayish yellow (91) | None |
| Glucose-asparagine agar | Moderate | Moderate; brownish black (65). Hygroscopic | Colorless | None |
| Bennett's agar | Moderate | Moderate; black. Hygroscopic | Grayish yellow (90) | None |

Observation after incubation at 28° C. for 3 weeks.
Color and number in parenthesis follow ISCC-NBS designation.

TABLE 2

Physiological characteristics of strain P247-71

| Hydrolysis of: | | Utilization of:* | |
|---|---|---|---|
| Gelatin | + | Glycerol | + |
| Starch: Soluble starch | + | D-Arabinose | ± |
| Potato starch | + | L-Arabinose | + |
| | | D-Xylose | ± |
| Milk coagulation | − | D-Ribose | + |
| peptonization | + | L-Rhamnose | + |
| Production of: | | D-Galactose | + |
| Nitrate reductase | − | D-Fructose | + |
| Tyrosinase | − | D-Mannose | − |
| | | L-Sorbose | − |
| Tolerance to: | | Sucrose | + |
| Lysozyme, 0.01% (w/v) | − | Lactose | + |
| 0.001% (w/v) | − | Cellobiose | + |
| NaCl, 1%-6% (w/v) | + | Melibiose | + |
| 7% (w/v) | − | Trehalose | ± |
| pH 5.5-10.5 | + | Raffinose | + |
| 5.0 and 11.0 | − | D-Melezitose | − |
| | | Soluble starch | + |
| Temperature: | | Cellulose | − |
| Growth range | 20° C.-39° C. | Dulcitol | − |
| No growth | 17° C. and 41° C. | Inositol | + |
| Optimal growth | 37° C.-39° C. | D-Mannitol | + |
| | | D-Sorbitol | − |
| | | Salicin | + |

*Basal medium: Pridham-Gottlieb's medium (= ISP No. 9 medium).

ism, e.g. 20° C. to 39° C., and is conveniently carried out at a temperature of about 28° C.

The fermentation may be carried out in flasks or in laboratory or industrial fermentors of various capacities. When tank fermentation is to be used, it is desirable to produce a vegetative inoculum in a nutrient broth by inoculating a small volume of the culture medium with a slant or soil culture or a lyophilized culture of the organism. After obtaining an active inoculum in this manner, it is transferred aseptically to the fermentation tank medium for large scale production of BU-3862T. The medium in which the vegetative inoculum is produced can be the same as, or different from, that utilized in the tank as long as it is such that a good growth of the producing organism is obtained.

In general, optimum production of BU-3862T is achieved after incubation periods of about four days.

BU-3862T may be recovered from the culture medium and isolated in a substantially pure form by conventional solvent extraction and chromatographic procedures. Example 2 below illustrates a suitable isolation and purification procedure.

The diacetate derivative (II) of BU-3862T may be prepared by reacting BU-3862T with a conventional acetylating agent such as acetic anhydride in an inert organic solvent. A typical procedure is illustrated in Example 3 below. The dihydro derivative (III) of BU-3862T may be prepared by catalytic hydrogenation of BU-3862T as illustrated in Example 4.

BU-3862T was obtained as a colorless sticky solid. It was readily soluble in dimethyl sulfoxide, dimethylformamide, methanol, ethanol, ethyl acetate and chloroform, but practically insoluble in water, benzene and other organic solvents.

Figure 2:
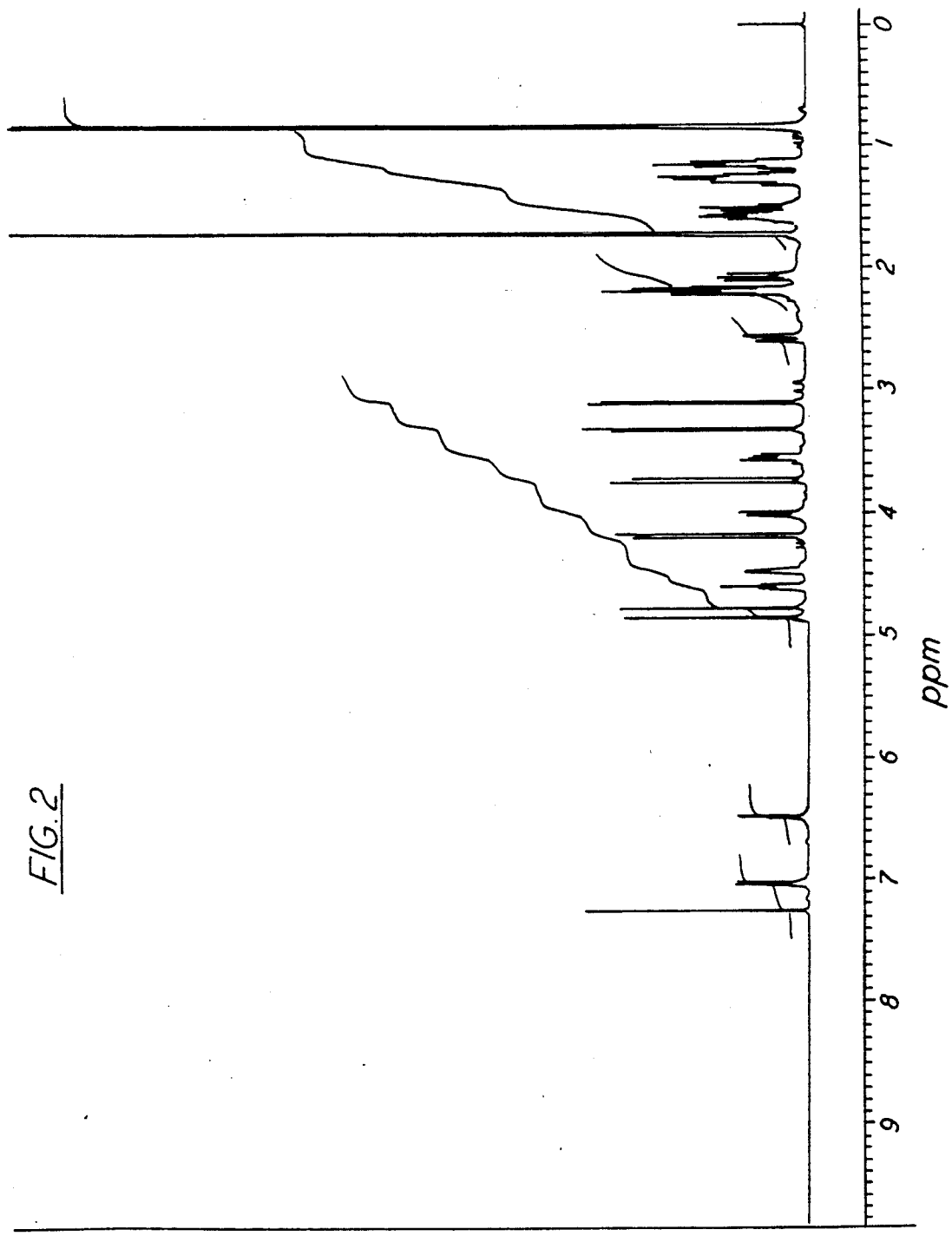
FIG. 2 represents the proton magnetic resonance spectrum of BU-3862T in $CDCl_3$ (400 MHz).
Figure 3:
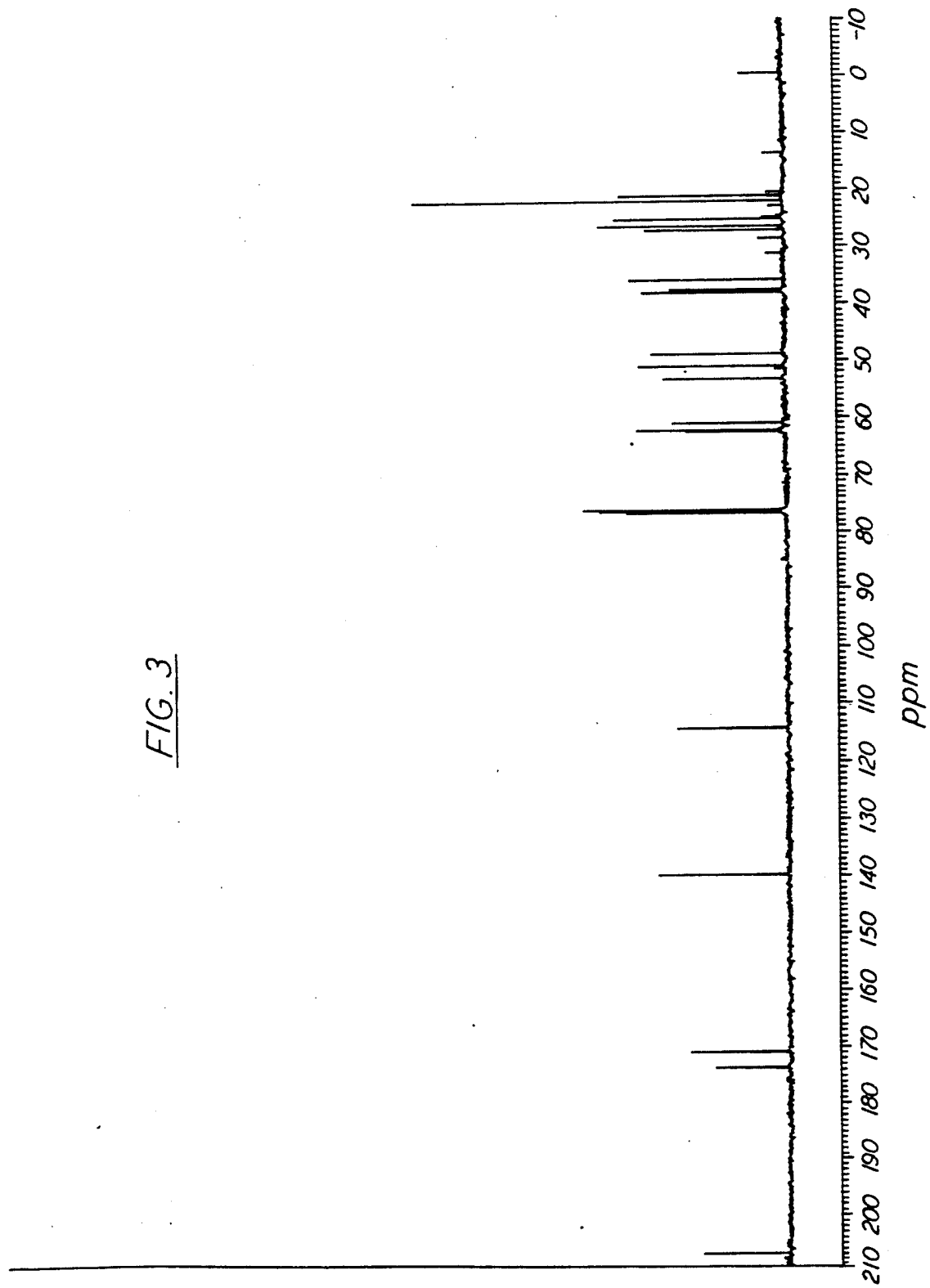
FIG. 3 represents the $^{13}C$ NMR spectrum of BU-3862T in $CDCl_3$ (100 MHz).

BU-3862T showed positive reaction to iodine, ammonium molybdate-sulfuric acid (AMS) and Rydone-Smith reagents, while it was negative to ninhydrin, anthrone and ferric chloride tests. The physico-chemical properties of BU-3862T are summarized in Table 3. This compound did not show characteristic UV absorption. The IR, $^1$H-NMR and $^{13}$C-NMR spectra of BU-3862T are illustrated in FIGS. 1, 2 and 3, respectively.

TABLE 3

| Physico-chemical properties of BU-3862T | |
|---|---|
| Nature: | Colorless sticky solid |
| $[\alpha]_D^{24}$: | +32 ±2° C. (c 0.5, methanol) |
| EI & FDMS: | m/z 399 (M + H)+ |
| Microanalysis: | Calcd for $C_{20}H_{34}N_2O_6$: C 60.28, H 8.60, N 7.03 |
| | Found: C 60.18, H 8.82, N 6.60 |
| TLC, SiO$_2$: | CH$_2$Cl$_2$—MeOH (9:1) Rf 0.37 |
| (Merck F$_{254}$) | EtOAc-13 MeOH (4:1) 0.59 |
| | Methylethylketone-Xylene-MeOH (10:10:2) 0.35 |

STRUCTURAL STUDIES ON BU-3862T

BU-3862T exhibits strong absorptions at 3300 (hydroxy), 1720 (carbonyl), 1650 and 1530 cm$^{-1}$ (amide) in the IR spectrum indicating a peptide structure for the antibiotic. The $^{13}$C-NMR spectrum demonstrated 20 carbons which were identified as two C—$\underline{\text{CH}}_3$, one =C—$\underline{\text{CH}}_3$, eight —$\underline{\text{CH}}_2$, three —$\underline{\text{CH}}$, one >$\underline{\text{C}}$<, one >$\underline{\text{C}}$=$\underline{\text{CH}}_2$ and three $\underline{\text{C}}$=O carbons. The molecular formula of BU-3862T was established as $C_{20}H_{34}N_2O_6$ based on the microanalysis, mass spectral data ((M+H)+: m/z 399) and $^{13}$C-NMR spectral analysis. Thirty-four protons were observed in the $^1$H-NMR spectrum. The two doublet protons (δ7.03 and 6.48 ppm, in CDCl$_3$) gradually disappeared by the addition of deuterium oxide were assigned to two —NH—CO groups. The broad two singlet protons (δ4.83 and 4.79) and the AB type doublet protons (δ3.35 and 3.12, J: 5.0 Hz) were assigned to exomethylene(—(CH$_3$)C=$\underline{\text{CH}}_2$) and epoxide

protons, respectively. The connectivities of these protons were determined by $^1$H-$^1$H COSY experiments leading to the partial structures as shown below. Further connectivities of the partial structures were established by the $^{13}$C-$^1$H COSY and $^{13}$C-$^1$H long range COSY experiments. They were analyzed as shown below and thus the total structure of BU-3862T was determined. Further evidence for the structure was provided by its mass spectrum and degradation experiment. The EI-MS spectrum exhibited abundant fragment ions at m/z 127 (iso-octanoyl), 214 (iso-octanoyl-seryl) and 325 (iso-octanoyl-seryl-4,5-didehydroleucyl) supporting the structure. Upon acid hydrolysis, BU-3862T gave an amino acid and a fatty acid. The amino acid isolated was identified as L-serine by HPLC and the fatty acid as iso-octanoic acid by gas chromatography of its methyl ester. BU-3862T afforded the diacetate derivative upon treatment with acetic anhydride in pyridine. When hydrogenated over palladium carbon, BU-3862T afforded two reduction products, dihydro-BU-3862T and tetrahydro-BU-3862T, whose structures were determined based on their spectral data. The diacetate and the dihydro compound retained the biological activity but the tetrahydro derivative was devoid of the activity.

BU-3862T may be named 1,2-epoxy-2-hydroxymethyl-4-(N-isooctanyl-L-serylamino)-6-methyl-hept-6-ene-3-one and is a unique peptide containing an epoxide and an exomethylene group.

Partial structures of BU-3862T

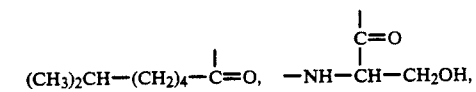

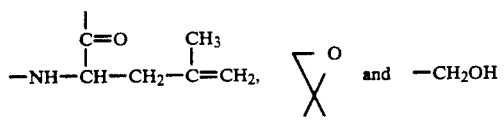

BU-3862T

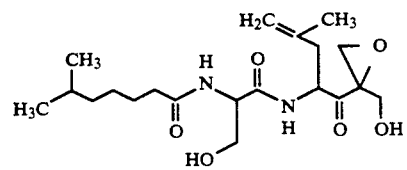

Diacetyl-BU-3862T

-continued

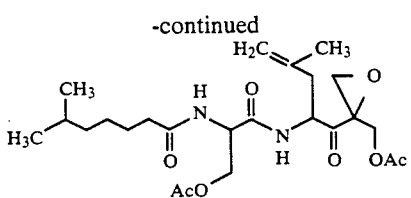
Dihydro-BU-3862T

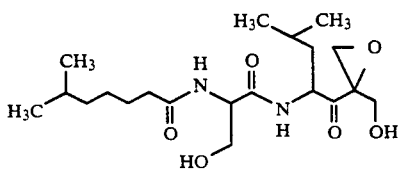
Tetrahydro-BU-3862T

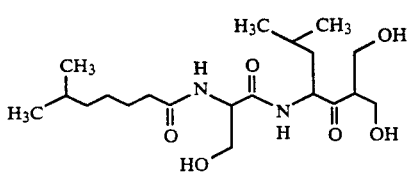

$^1$H-$^1$H and $^{13}$C-$^1$H long range NMR spectra

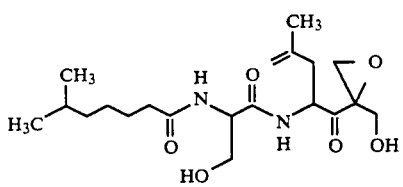

⟶ $^1$H-$^1$H long range

⟶ $^{13}$C-$^1$H long range

BIOLOGICAL ACTIVITY OF BU-3862T

BU-3862T and diacetyl-, dihydro- and tetrahydro-BU-3862T were tested for in vitro cytotoxicity against several murine and human tumor cell lines and/or for in vivo antitumor activity in mice. Mitomycin C was used as a reference compound in both in vitro and in vivo experiments. B16-F10 (murine melanoma), P388 (murine leukemia), L1210 (murine leukemia) and Moser (human colorectal carcinoma) cells were grown to the logarithmic phase in enriched Eagle minimum essential medium (MEM) supplemented with fetal calf serum (FCS, 10%) and kanamycin (60 mcg/ml), and HCT-116 (human colon carcinoma) cells in Maccoy's 5A medium supplemented with FCS (10%), penicillin (100 u/ml) and streptomycin (100 mcg/ml), harvested and inoculated into wells of the 96- or 24-well tissue culture plate with test materials at the concentrations of $1.5 \times 10^5$, $1.2 \times 10^4$, $1.2 \times 10^4$, $2.5 \times 10^5$ and $3.0 \times 10^5$ cells/ml, respectively. They were incubated at 37° C. in humidified atmosphere of 5% $CO_2$ and 95% air for 72 hours. The cytotoxic activities against B16-F10, Moser and HCT-116 cells were colorimetrically determined at 540 nm after staining viable cells with 0.006% neutral red solution. On the other hand, the cytotoxic activities against P388 and L1210 cells were determined by counting the number of viable cells. The results were summarized in Table 4. Compared with mitomycin C, BU-3862T showed much more potent cytotoxicity against both murine and human cells. The potency was approximately 50–120 times greater than that of mitomycin C in terms of $IC_{50}$ values. The diacetyl and dihydro derivatives also showed equivalently potent cytotoxic potentials against both murine and human cells, approximately half those of BU-3862T. On the other hand, the tetrahydro derivative was significantly less active than the above compounds.

Inhibitory effects of BU-3862T on macromolecule (DNA, RNA and protein) synthesis were determined in cultured B16-F10 melanoma cells. B16-F10 cells ($10^5$ cells/ml) were incubated with BU-3862T at 37° C. for 3.5 (for DNA synthesis) or 4 (for RNA and protein synthesis) hours. Isotopically labelled precursor, $^3$H-thymidine, $^{14}$C-uridine or $^3$H-leucine was added into the cultured mixture and further incubated for 30 min (for DNA synthesis) or 60 min (for RNA and protein synthesis). After washing with chilled 5% trichloroacetic acid solution, the radioactivity incorporated into the acid-insoluble fraction of the tumor cells was determined in a liquid scintillation counter. As shown in Table 5, BU-3862T inhibited both DNA and protein synthesis similarly and the potency was over 100 times higher than that on RNA synthesis in terms of IC50 value.

In vivo antitumor activities of BU-3862T and the diacetyl and dihydro derivatives were determined in tumor-bearing $BDF_1$ or $CDF_1$ mice. Male $BDF_1$ mice were intraperitoneally inoculated with 0.5 ml of 10% melanotic melanoma B16 brei and female $CDF_1$ mice were also intraperitoneally inoculated with 0.4 ml of diluted ascitic fluid containing $10^5$ lymphoid leukemia L1210 cells or $10^6$ lymphocytic leukemia P388 cells. Test compounds were intraperitoneally administered to the mice by the following four different treatment schedules; once a day on days 1, 2 and 3 (QD×3), on days 1, 4 and 7 (Q3D×3), on days 1, 5 and 9 (Q4D×3) and on days 1 to 9 (QD×9). As shown in Table 6, BU-3862T demonstrated an excellent therapeutic efficacy against B16 melanoma. When administered by the Q4D×3 treatment schedule, the potency (minimum effective dose) of BU-3862T was the same as that of mitomycin C. This compound showed better antitumor activity and broader therapeutic range by the intermittent dosing schedule (Q4D×3) than by the consecutive dosing schedule (QD×9) in terms of maximum T/C value and chemotherapeutic index (ratio of optimal dose to minimum effective dose), respectively. Both the diacetyl and dihydro derivatives also exhibited significant anti-B16 melanoma activity by the Q4D×3 treatment schedule but were approximately ten times less active than the parent compound in terms of minimum effective dose as shown in Table 7. On the other hand, anti-leukemic activities of BU-3862T were rather weak. This compound gave moderate antitumor activity against L1210 leukemia with maximum T/C value of 145% and showed no significant prolongation of lifespan in P388 leukemia-bearing mice at the doses tested (Tables 8 and 9).

TABLE 4

| In vitro cytotoxicities aainst murine and human tumor cells | | | | | |
|---|---|---|---|---|---|
| | $IC_{50}$ (mc/ml) | | | | |
| Comound | B16-F10 | P388 | L1210 | HCT-116 | Moser |
| BU-3862T | 0.0017 | 0.031 | 0.01 | 0.0097 | 0.016 |
| Diacetyl-BU-3862T | 0.0030 | ND* | ND | 0.017 | 0.044 |
| Dihydro- | 0.0032 | ND | ND | 0.013 | 0.038 |

TABLE 4-continued

In vitro cytotoxicities aainst murine and human tumor cells

| Comound | IC$_{50}$ (mc/ml) | | | | |
|---|---|---|---|---|---|
| | B16-F10 | P388 | L1210 | HCT-116 | Moser |
| BU-3862T Tetrahydro-BU-3862T | 0.53 | ND | ND | >1.0 | >1.0 |
| Mitomycin C | 0.50 | ND | ND | 0.80 | 1.2 |

*ND: Not determined

TABLE 5

Inhibition of macromolecule synthesis in B16 melanoma cells

| Compound | IC$_{50}$ (mc/ml) | | |
|---|---|---|---|
| | DNA | RNA | Protein |
| BU-3862T | 0.10 | 11 | 0.060 |
| Mitomycin C | 1.6 | 11 | 60 |

TABLE 6

Antitumor activity of BU-3862T against B16 melanoma (ip)

| Compound | Dose (mg/kg/day) | Treatment schedule (ip) | MST*1 (day) | T/C (%) | Body wt. change on day 5 (g) |
|---|---|---|---|---|---|
| BU-3862T | 8.0 | Q4D × 3 | 20.0 | 167*2 | −2.3 |
| | 4.0 | " | 19.0 | 158*2 | −1.3 |
| | 2.0 | " | 18.0 | 150*2 | −0.5 |
| | 1.0 | " | 17.0 | 142*2 | +0.3 |
| | 0.5 | " | 15.5 | 129*2 | +0 5 |
| | 0.25 | " | 14.0 | 117 | +0.5 |
| Mitomycin C | 2.0 | Q4D × 3 | 29.0 | 242*2 | +0.3 |
| | 1.0 | " | 18.5 | 154*2 | +0.5 |
| | 0.5 | " | 15.0 | 125*2 | +0.5 |
| | 0.25 | " | 13.0 | 108 | +0.3 |
| Vehicle | — | Q4D × 3 | 12.0 | — | +1.1 |
| BU-3862T | 2.0 | QD × 9 | Tox. | Tox. | — |
| | 1.0 | " | 14.5 | 97 | −3.3 |
| | 0.5 | " | 20.0 | 133*2 | −2.3 |
| | 0.25 | " | 20.0 | 133*2 | +0.3 |
| | 0.13 | " | 18.5 | 123 | +0.8 |
| | 0.63 | " | 18.0 | 113 | +1.3 |
| Vehicle | — | QD × 9 | 15.0 | — | +1.3 |

*1Median survival time
*2Significant antitumor effect (T/C ≧ 125%)

TABLE 7

Antitumor activity of diacetyl- and dihydro- BU-3862T against B16 melanoma (ip)

| Compound | Dose (mg/kg/day) | Treatment schedule (ip) | MST*1 (day) | T/C (%) | Body wt. change on day 5 (g) |
|---|---|---|---|---|---|
| Diacetyl-BU-3862T | 8.0 | Q4D × 3 | 24.0 | 141*2 | −2.0 |
| | 4.0 | " | 23.0 | 135*2 | +0.5 |
| | 2.0 | " | 20.5 | 121 | +1.0 |
| | 1.0 | " | 20.0 | 118 | +0.3 |
| | 0.5 | " | 19.0 | 112 | +1.3 |
| Dihydro-BU-3862T | 8.0 | Q4D × 3 | 22.5 | 132*2 | −1.0 |
| | 4.0 | " | 20.0 | 118 | −0.5 |
| | 2.0 | " | 21.0 | 124 | +0.5 |
| | 1.0 | " | 19.5 | 115 | +0.5 |
| | 0.5 | " | 19.0 | 112 | +0.5 |
| Mitomycin C | 2.0 | Q4D × 3 | 33.0 | 194*2 | 0.0 |
| | 1.0 | " | 23.0 | 135*2 | +1.0 |
| | 0.5 | " | 22.0 | 129*2 | +0.3 |
| | 0.25 | " | 20.0 | 118 | +0.3 |
| Vehicle | — | Q4D × 3 | 17.0 | — | +0.8 |

*1Median survival time
*2Significant antitumor effect (T/C ≧ 125%)

TABLE 8

Antitumor activity of BU-3862T against L1210 leukemia (ip)

| Compound | Dose*1 (mg/kg/day) | MST*2 (day) | T/C (%) | Body wt. change on day 5 (g) |
|---|---|---|---|---|
| BU-3862T | 4.0 | Tox. | Tox. | — |
| | 2.0 | 11.5 | 144*3 | −3.5 |
| | 1.0 | 10.0 | 125*3 | −2.8 |
| | 0.5 | 9.5 | 119 | −0.8 |
| | 0.25 | 9.5 | 119 | 0.0 |
| Mitomycin C | 2.0 | 13.0 | 163*3 | −0.5 |
| | 1.0 | 11.0 | 138*3 | −0.3 |
| | 0.5 | 10.5 | 131*3 | 0.0 |
| | 0.25 | 10.0 | 125*3 | +0.8 |
| Vehicle | — | 8.0 | — | +1.1 |

*1Q3D × 3, ip for BU-3862T and QD × 3, ip for mitomycin C
*2Median survival time
*3Significant antitumor effect (T/C ≧ 125%)

TABLE 9

Antitumor activity of BU-386ZT against P388 leukemia (ip)

| Compound | Dose*1 (mg/kg/day) | MST*2 (day) | T/C (%) | Body wt. change on day 5 (g) |
|---|---|---|---|---|
| BU-3862T | 4.0 | 11.0 | 105 | −2.3 |
| | 2.0 | 11.0 | 105 | −2.8 |
| | 1.0 | 11.5 | 110 | −0.8 |
| | 0.5 | 13.0 | 124 | −0.3 |
| | 0.25 | 12.5 | 119 | +0.8 |
| Mitomycin C | 2.0 | 17.0 | 162*3 | +1.5 |
| | 1.0 | 15.0 | 143*3 | +1.8 |
| | 0.5 | 13.0 | 124 | +1.8 |
| | 0.25 | 13.0 | 124 | +2.3 |
| Vehicle | — | 10.5 | — | +2.4 |

*1Q4D × 3, ip
*2Median survival time
*3Significant antitumor effect (T/C ≧ 125%)

As indicated by the data shown above, BU-3862T and its dihydro and diacetyl derivatives are useful as antitumor agents for inhibition of mammalian malignant tumors such as B16 melanoma.

The invention includes within its scope pharmaceutical compositions containing an effective tumor-inhibiting amount of BU-3862T, dihydro-BU-3862T or diacetyl-BU-3862T in combination with an inert pharmaceutically acceptable carrier or diluent. Such compositions may also contain other active antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixers and preparations for parenteral administration such as sterile solutions, suspensions or emulsions. They may also be manufactured in the form of sterile solid compositions which can be dissolved in sterile water, physiological saline or other suitable sterile injectable medium immediately before use.

For use as an antitumor agent, optimal dosages and regimens of BU-3862T or its dihydro or diacetyl derivative for a given mammalian host can be readily ascertained by those skilled in the art. It will, of course, be appreciated that the actual dose of compound used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are provided for illustrative purposes only and are not intended to limit the scope of the invention.

EXAMPLE 1

Fermentation of BU-3862T

A well grown agar slant of *Streptomyces hygroscopicus*, Strain No. P247-71, was used to inoculate a vegetative medium consisting of 3% soybean meal (Nikko Seiyu), 0.5% Pharmamedia (Traders, U.S.A.), 3% glucose, 0.1% yeast extract (Oriental) and 0.3% $CaCO_3$, the pH being adjusted to 7.0 before sterilization. The vegetative medium was incubated at 28° C. for 4 days on a rotary shaker (200 rpm) and 5 ml of the growth was transferred into a 500-ml Erlenmeyer flask containing 100 ml of the fermentation medium having the same composition as the vegetative medium. The fermentation was carried out at 28° C. for 4 to 5 days with shaking on the rotary shaker.

The antitumor antibiotic production in the fermentation broth was determined by in vitro cytotoxic activity against B16 melanoma cells. The fermentation was also carried out in a tank fermentor. A 2-liter portion of the vegetative culture by the flask fermentation was transferred into a 200-liter tank fermentor containing 120 liters of the fermentation medium. Fermentation was run at 28° C. with agitation at 250 rpm and aeration rate of 120 liters per minute. The antitumor antibiotic level reached a maximum of 50 µg/ml after about 90 hours fermentation.

EXAMPLE 2

Isolation and Purification of BU-3862T

The fermentation broth (23 L, pH 7.4) obtained by the general procedure of Example 1 was separated into the mycelial cake and the supernate by use of a Sharpless-type centrifuge (Kokusan No. 4A). The mycelial cake was extracted with methanol (6 L). After removal of the insolubles by filtration, the methanolic extract was concentrated in vacuo to an aqueous solution. This aqueous solution and the supernate of the fermentation broth were combined and extracted with ethyl acetate (20 L). The extract was evaporated to dryness in vacuo yielding 21.1 g of crude antibiotic complex. This crude solid was applied on a column of silica gel ($\phi 4.0 \times 75$ cm) which had been pre-washed with methylene chloride, and was developed by a methylene chloride-methanol mixture with stepwise increase of methanol concentration (2–10% v/v). The eluant was monitored by cytotoxicity against B16 melanoma and color reaction with iodine on a TLC plate. The first iodine positive fractions eluted with 2% methanol were collected and further purified by Sephadex LH-20 chromatography. The purified component was identified as 9-methylstreptimidone[1] on the basis of its spectral data. The second iodine positive fractions eluted with 5% methanol were collected and evaporated in vacuo to afford semi-pure solid of BU-3862T. This was further chromatographed on silica gel using ethyl acetate-methanol mixture. Elution with the mixture of 50:1 v/v ratio gave active fractions which showed strong cytotoxicity against B16 melanoma. After concentration in vacuo, the residue was further purified by Sephadex LH-20 chromatography with methanol elution to afford a homogeneous solid of BU-3862T (341 mg).

1) Saito, N.; F. Kitame, M. Kikuchi and N. Ishida: Studies on a new antiviral antibiotic, 9-methylstreptimidone. 1. Physicochemical and biological properties. J. Antibiotics 27: 206–214, 1974.

EXAMPLE 3

Preparation of Diacetyl-BU-3862T

BU-3862T (10 mg) was stirred with acetic anhydride (0.1 ml) and dry pyridine (0.5 ml) for 18 hours at room temperature. The reaction mixture was diluted with ethyl acetate (10 ml), and the solution was washed with dilute HCl (10 ml) and then water (10 ml). The organic solution was dried over $Na_2SO_4$ and evaporated in vacuo to give oily diacetyl BU-3862T (13 mg). Physicochemical properties are listed in Tables 9 and 10 below.

TABLE 9

| | Physico-chemical Properties of BU-3862T Derivatives | | |
|---|---|---|---|
| | Diacetyl-BU-3862T | Dihydro-BU-3862T | Tetrahydro-BU-3862T |
| Nature | Colorless sticky solid | Colorless sticky solid | Colorless sticky solid |
| SIMS m/z | 483 (M + H)+ | 401 (M + H)+ | 403 (M + H)+ |
| EIMS m/z | 423 (M—$COOCH_3$)+ | 370 (M + H—$CH_2OH$)+ | 372 (M + H—$CH_2OH$)+ |
| | 430 | 299 | 299 |
| | 256 | 214 | 214 |
| | 127 | 127 | 127 |
| IR $\nu$KBr $cm^{-1}$ max | 3300 | 3300 | 3300 |
| | 3070 | 3070 | 3070 |
| | 2950 | 2950 | 2950 |
| | 1750 | 1720 | 1710 |
| | 1650 | 1640 | 1640 |
| | 1550 | 1530 | 1530 |
| | 1240 | 1050 | 1050 |
| | 1040 | | |
| TLC, $SiO_2$ Rf $CH_2Cl_2$—MeOH (9:1) | 0.78 | 0.37 | 0.21 |

TABLE 10

$^1$H-NMR Data of Bu-3862T and Its Derivatives (400 MHz in $CDCl_3$)

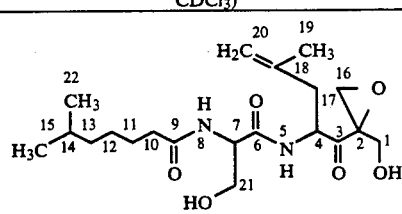

| Position No. | BU-3862T | Diacetyl-BU-3862T | Dihydro-BU-3862T | Tetrahydro-BU-3862T |
|---|---|---|---|---|
| 1 | 3.75 (d) | 4.01 (d) | 3.73 (d) | 3.74 (dd)[a] |
| | 4.21 (d) | 4.87 (d) | 4.21 (d) | 3.90 (m) |
| 2 | — | — | — | 3.15 (m) |
| 4 | 4.61 (ddd) | 4.61 (ddd) | 4.51 (m) | 4.58 (m)[b] |

TABLE 10-continued $^1$H-NMR Data of Bu-3862T and Its Derivatives (400 MHz in CDCl$_3$)

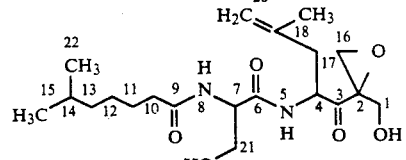

| Position No. | BU-3862T | Diacetyl-BU-3862T | Dihydro-BU-3862T | Tetrahydro-BU-3862T |
| --- | --- | --- | --- | --- |
| 5 | 7.03 (d) | 6.53 (d) | 7.10 (d) | 7.31 (d) |
| 7 | 4.48 (ddd) | 4.70 (ddd) | 4.49 (ddd) | 4.54 (m)$^{b)}$ |
| 8 | 6.48 (d) | 6.22 (d) | 6.51 (d) | 6.52 (d) |
| 10 | 2.21 (t) | 2.21 (t) | 2.22 (t) | 2.24 (t) |
| 11 | 1.60 (m) | 1.59 (m) | 1.60 (m) | 1.61 (m) |
| 12 | 1.28 (m) | 1.28 (m) | 1.28 (m) | 1.29 (m) |
| 13 | 1.16 (m) | 1.18 (m) | 1.16 (m) | 1.19 (m) |
| 14 | 1.52 (m) | 1.52 (m) | 1.52 (m) | 1.52 (m) |
| 15 | 0.86 (d) | 0.86 (d) | 0.85 (d) | 0.86 (d) |
| 16 | 3.12 (d) | 3.09 (d) | 3.10 (d) | 3.81 (dd)$^{a)}$ |
|  | 3.35 (d) | 3.38 (d) | 3.31 (d) | 3.90 (m) |
| 17 | 2.08 (dd) | 2.07 (dd) |  |  |
|  | 2.59 (dd) | 2.60 (dd) | 1.28 (m) | 1.29 (m) |
| 18 | — | — | 1.66 (m) | 1.70 (m) |
| 19 | 1.75 (s) | 1.76 (s) | 0.94 (d)$^{c)}$ | 0.96 (d)$^{d)}$ |
| 20 | 4.79 (brs) | 4.80 (brs) | 0.95 (d)$^{c)}$ | 0.97 (d)$^{d)}$ |
|  | 4.83 (brs) | 4.88 (brs) |  |  |
| 21 | 3.58 (dd) | 4.18 (dd) | 3.58 (dd) | 3.59 (dd) |
|  | 4.02 (dd) | 4.37 (dd) | 4.03 (dd) | 4.06 (dd) |
| 22 | 0.86 (d) | 0.86 (d) | 0.85 (d) | 0.86 (d) |
| OCOCH$_3$ |  | 2.05, 2.09 |  |  |

$^{a)}$, $^{b)}$, $^{c)}$ and $^{d)}$ indicate pairs of assignments that may be interchanged

EXAMPLE 4

Preparation of Dihydro- and Tetrahydro-BU-3862T

Bu-3862T (30 mg) dissolved in methanol (10 ml) was hydrogenated under atmospheric pressure in the presence of 20% Pd/C (15 mg) for 20 hours. The reaction mixture was filtered and the filtrate was evaporated under reduced pressure to afford a mixture of two hydrogenation products (27 mg). They were separated by preparative TLC (SiO$_2$, CH$_2$Cl$_2$—MeOH=9:1 v/v) and purified by Sephadex LH-20 chromatography to obtain dihydro (13.4 mg) and tetrahydro BU-3862T (4.7 mg). Physico-chemical properties are shown in Tables 9 and 10 above.

We claim:

1. A process for producing BU-3862T of the formula

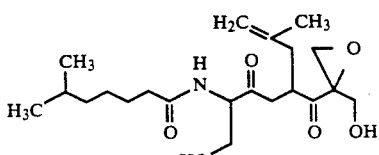

which comprises cultivating *Streptomyces hygroscopicus* ATCC 53709 in an aqueous nutrient medium containing assimilable sources of carbon and nitrogen under submerged aerobic conditions until a recoverable amount of BU-3862T is produced by said organism in said culture medium and then recovering said BU-3862T from the culture medium.

* * * * *